United States Patent [19]
Nestell

[11] Patent Number: 5,925,020
[45] Date of Patent: Jul. 20, 1999

[54] NEEDLE POINT BARRIER

[75] Inventor: Bengt Nestell, Pottstown, Pa.

[73] Assignee: Becton, Dickinson and Company, Franklin Lakes, N.J.

[21] Appl. No.: 08/343,798

[22] Filed: Nov. 22, 1994

[51] Int. Cl.[6] .................................................. A61M 5/32
[52] U.S. Cl. .......................... 604/198; 604/263; 128/919
[58] Field of Search .................................. 604/268, 192, 604/110, 196, 197, 198, 263; 128/919

[56] References Cited

U.S. PATENT DOCUMENTS

| | | | |
|---|---|---|---|
| 4,867,172 | 9/1989 | Haber et al. | 128/763 |
| 4,935,013 | 6/1990 | Haber et al. | 604/192 |
| 5,348,544 | 9/1994 | Sweeney et al. | 604/192 |

*Primary Examiner*—Ronald Stright, Jr.
*Assistant Examiner*—A. T. Nguyen
*Attorney, Agent, or Firm*—John L. Voellmicke

[57] ABSTRACT

A needle point barrier includes a resiliently deflectable spring arm, a link arm and a barrier arm. The proximal end of the spring arm is secured near the proximal end of the needle. The link arm has one end hingedly connected to the spring arm and an opposed end hingedly connected to a proximal position on the barrier arm. Distal portions of the barrier arm slidably engage the needle. The needle point barrier can be collapsed into a Z-shaped configuration near the proximal end of the needle. The barrier arm can be urged distally by force applied to the proximal end of the barrier arm. Initial movement of the barrier arm will deflect the spring arm away from the needle. After sufficient manual movement of the barrier arm, the resiliency of the spring arm will urge the barrier arm distally into shielding relationship with the distal end of the needle.

20 Claims, 3 Drawing Sheets

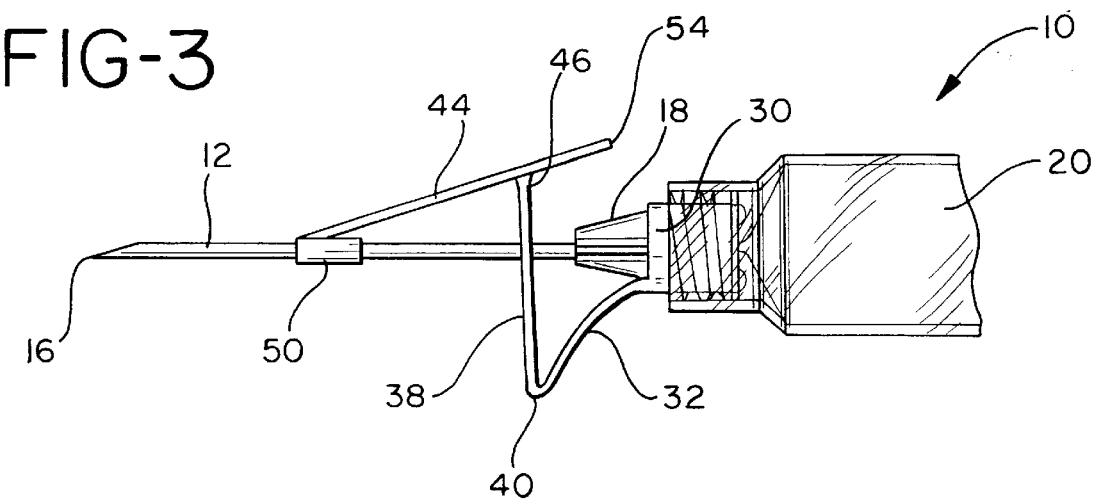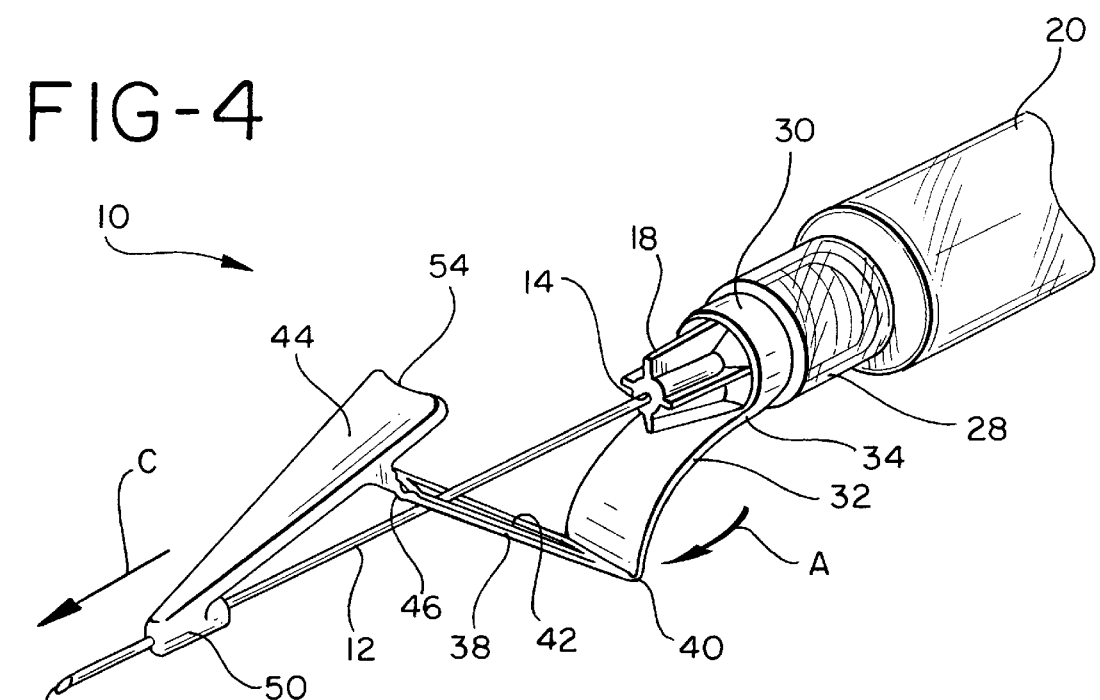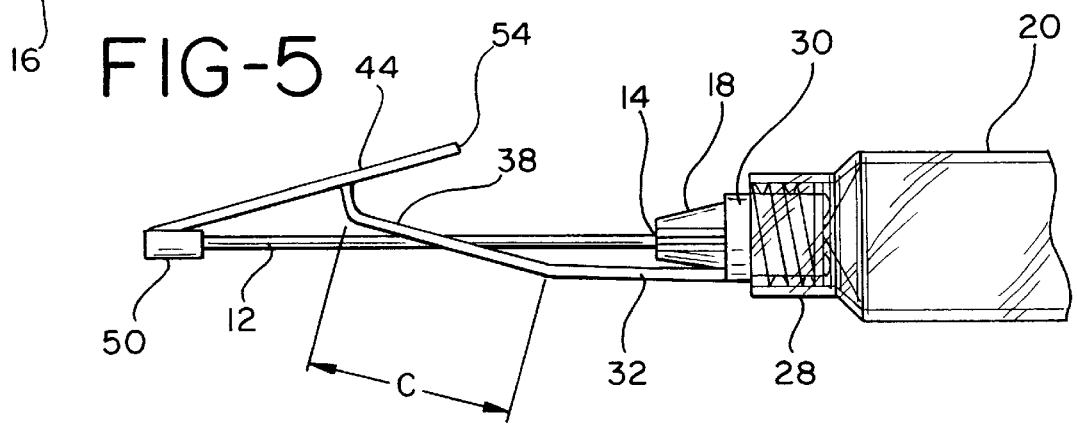

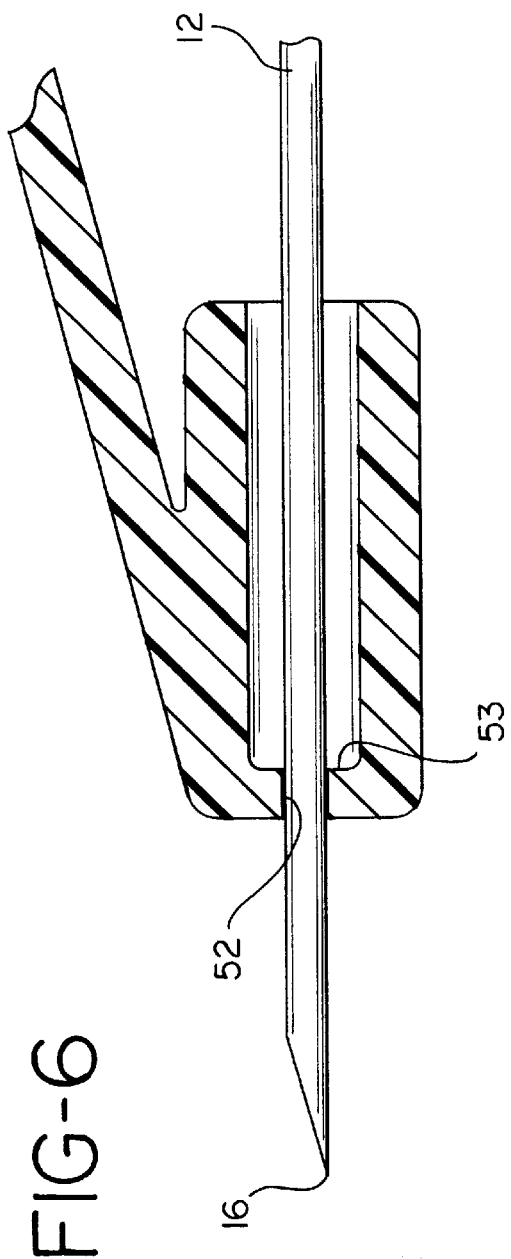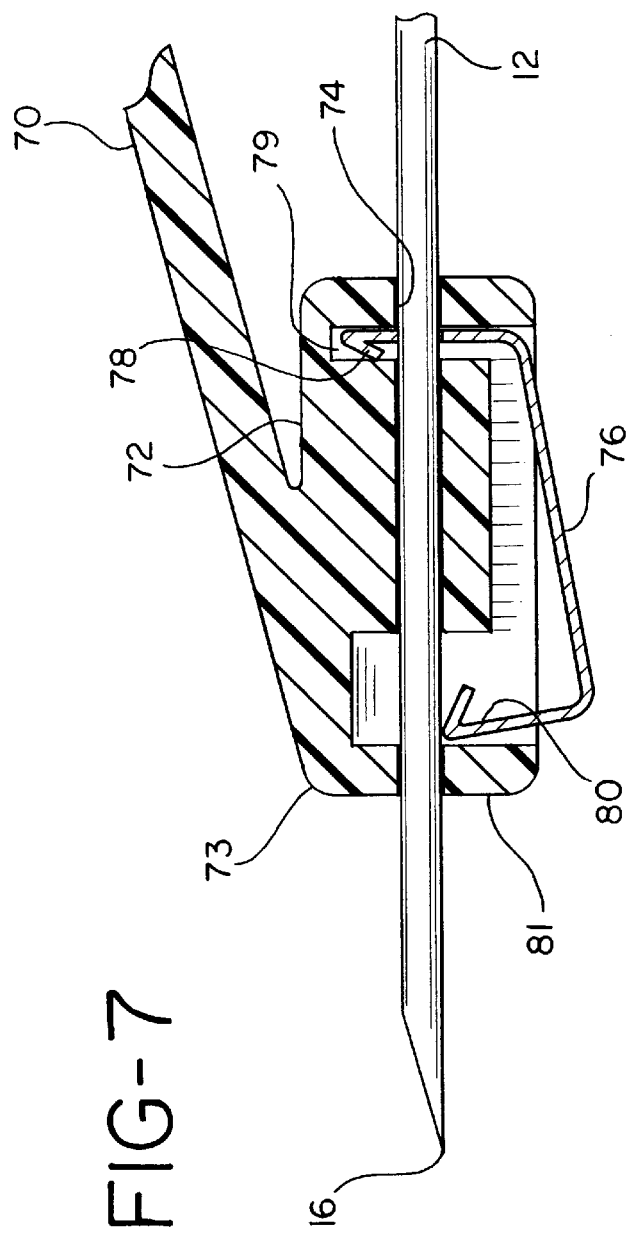

NEEDLE POINT BARRIER

BACKGROUND OF THE INVENTION

1. Field of the Invention

The subject invention relates to a needle point barrier which, after an initial manual movement, is self-propelled into shielding relationship with the needle point. The needle point barrier is capable of single-handed actuation.

2. Description of the Prior Art

Prior art needles include a proximal end that can be mounted to a medical implement and a sharply pointed distal end that can be used to administer drugs to a patient or to extract bodily fluids from a patient. Accidental sticks with a used needle have the potential to transmit disease. As a result, prior art needles and medical implements such as syringes and blood collection tube holders are provided with safety shields.

Some prior art shields define an elongate rigid tube that is telescoped over the hypodermic syringe or blood collection tube holder to which a needle is attached. This prior art medical implement is shielded by holding proximal portions of the implement in one hand and the shield in the other hand. The shield is then moved distally relative to the medical implement into a position where the needle is safely surrounded. Prior art shields of this type require two-handed actuation.

Some prior art shields include coil springs to urge the shield distally. However, it is undesirable to lock a coiled spring in a compressed state due to the possibility of the shield misfiring during use of the needle. Additionally, plastic parts stored in a preloaded condition can deform over time.

U.S. Pat. No. 5,242,417 teaches a syringe guard integrally connected to a hypodermic syringe by an over-center hinge. The guard extends orthogonally to the syringe axis during use of the syringe. After use, however, the guard can be rotated approximately 90° into surrounding relationship with the needle of the syringe. Although this guard enables single-handed actuation, the orthogonal alignment of the guard prior to actuation creates a visual obstruction and can physically interfere with normal use of the syringe.

SUMMARY OF THE INVENTION

The subject invention is directed to a needle point barrier for a needle cannula having a proximal end and a sharply pointed distal end. The proximal end of the needle cannula may be securely embedded in a needle hub that may be removably engageable with a hypodermic syringe or other medical implement.

The needle point barrier of the subject invention includes a spring arm having opposed proximal and distal ends. The proximal end of the spring arm is secured near the proximal end of the needle cannula. The distal end of the spring arm projects a portion of the distance toward the distal end of the needle cannula. The spring arm, in an unbiased condition, may be substantially parallel to the needle cannula. However, distal portions of the spring arm can be biased away from the needle cannula.

A link arm is hingedly connected to the distal end of the spring arm. The link arm may include an elongate slot through which the needle cannula and portions of the needle hub may extend.

The needle point barrier further includes a barrier arm with opposed proximal and distal ends. The proximal end of the barrier is hingedly connected to the end of the link arm remote from the spring arm. The distal end of the barrier arm defines a tip guard slidably engaged around the needle cannula.

In a ready-to-use position of the needle point barrier, the tip guard of the barrier arm is disposed proximally on the needle cannula and substantially adjacent the distal end of the spring arm. After use, distally directed forces may be exerted on the proximal end of the barrier arm with a thumb or forefinger of the hand holding the medical implement. These forces simultaneously urge the barrier arm distally along the needle cannula, rotate the link arm and urge the distal end of the spring arm away from the needle cannula. These manual forces are exerted until the barrier arm is distally beyond the spring arm. At this position the resiliency of the spring arm will further rotate the link arm and help propel the barrier arm distally. Distal movement of the barrier arm will terminate when the spring arm, the link arm and the barrier arm assume an approximately linear alignment relative to one another. The relative dimensions of the barrier arm, the link arm and the spring arm are selected to ensure that the tip guard of the barrier arm protectively surrounds the distal end of the needle cannula when the hingedly connected members of the needle barrier are in their approximately linear alignment relative to one another.

The needle point barrier of the subject invention offers several significant advantages. First, the double-hinged construction ensures that the entire barrier will be visually and physically unobtrusive during normal usage of the medical instrument. Additionally, the needle point barrier is stable both in the ready-to-use condition of the needle cannula and in the fully shielded condition thereof. Thus, no portions of the needle point barrier are required to maintain a stored energy prior to and during use of the needle cannula. This absence of stored energy enables the needle point barrier to be formed substantially entirely from plastic material that may be molded unitarily with a needle hub or attached to a needle hub.

BRIEF DESCRIPTION OF THE DRAWINGS

FIG. 3 is a side elevational view similar to FIG. 1, but showing the needle point barrier with the link arm aligned orthogonally to the needle cannula.

FIG. 4 is a perspective view similar to FIG. 1, but showing the tip guard being propelled toward the distal end of the needle.

FIG. 5 is a side elevational view similar to FIG. 3, but showing the needle point barrier shielding the distal end of the needle.

FIG. 6 is a partial cross-sectional view of the tip guard of the needle point barrier of the subject invention.

FIG. 7 is a partial cross-sectional view of an alternative tip guard of the needle point barrier of the subject invention.

DETAILED DESCRIPTION OF THE PREFERRED EMBODIMENT

Figure 1:
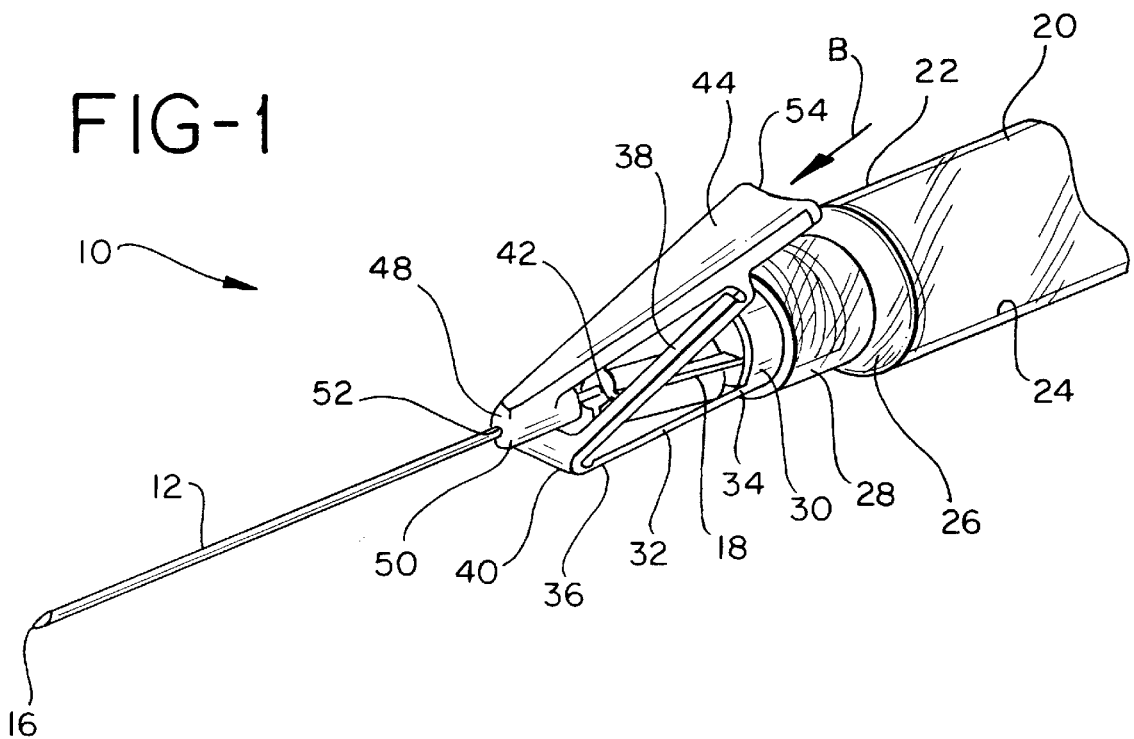
FIG. 1 is a perspective view of a hypodermic syringe incorporating the needle point barrier of the subject invention.

A needle point barrier in accordance with the subject invention is identified generally by the numeral 10 in FIGS. 1–5. Needle point barrier 10 is used with a needle cannula 12 having a proximal end 14 and a sharply pointed distal end 16. Proximal end 14 of needle cannula 12 is securely connected to needle hub 18.

Figure 2:
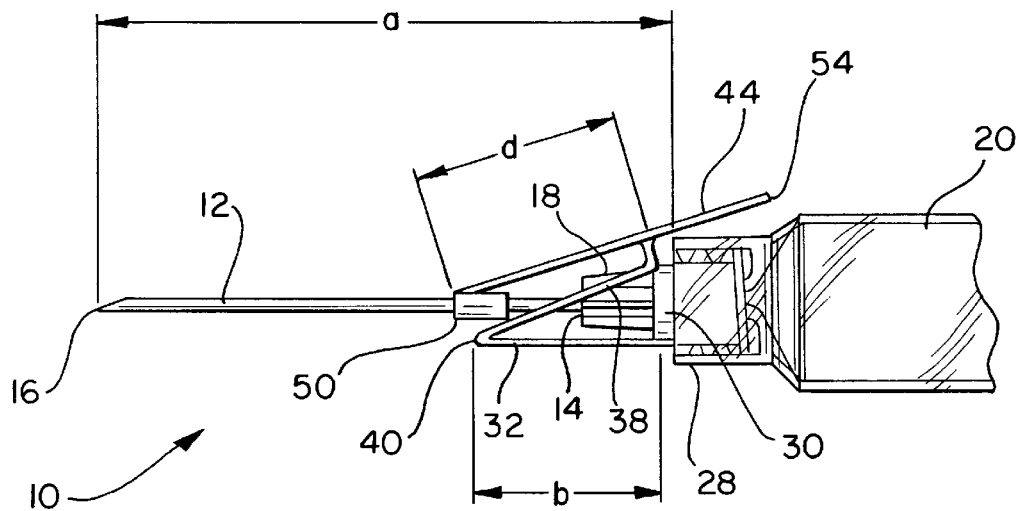
FIG. 2 is a side elevational view of the hypodermic syringe shown in FIG. 1.

The assembly of needle cannula 12 and needle hub 18 are selectively engageable with a hypodermic syringe 20. More particularly, syringe 20 includes an elongate barrel 22 with a fluid receiving chamber 24 therein. Syringe barrel 22 includes a distal end characterized by a tip (not shown) with a passageway extending therethrough and into communication with chamber 24. Distal end 26 of syringe barrel 22 can also include a luer collar 28 which surrounds the tip and includes an internal thread. Needle hub 18 is selectable engageable and disengageable from luer collar 28 so that the lumen through needle cannula 12 can be placed in communication with fluid receiving chamber 24 of syringe barrel 22. As shown in FIG. 2, needle 12 projects a distance "a" from luer collar 28.

In the embodiment illustrated herein, needle point barrier 10 can be uinitarily molded from a plastic material and is connected to needle hub 18 or unitarily molded with the needle hub. In this embodiment, element 30 in FIG. 1 defines a mounting collar that can be connected to the hub such as by a snapped into engagement with an undercut formed on needle hub 18. Other means such as adhesive and ultrasonic welding may be used to connect the collar to the hub. Thus, in this embodiment, needle point barrier 10 may be formed from metal or from a plastic material that is separate from the needle hub 18.

Needle point barrier 10 includes a spring arm 32 having opposed proximal and distal ends 34 and 36. Spring arm 32 defines an axial length "b", as shown in FIG. 2, approximately equal to one-third the length projection "a" of needle cannula 12 from luer collar 28. Proximal end 34 of spring arm 32 is preferably non-rotatably joined to needle hub 18 near the extreme distal end of luer collar 28. In the condition depicted in FIGS. 1 and 2, spring arm 32 is substantially planar and is aligned substantially parallel to needle cannula 12. However, spring arm 32 is formed from a deflectable resilient material. Therefore, distal end 36 of spring arm 32 can be deflected away from needle cannula 12 as shown in FIGS. 3 and 4. In response to such deflection, spring arm 32 will exert resiliently generated biasing forces in the direction indicated by arrow "A" in FIG. 4.

Needle point barrier 10 further includes link arm 38 which is unitarily articulated to spring arm 32 at a hinge line 40. Hinge line 40 is orthogonal to needle cannula 12. Link arm 38 includes a longitudinally extending slot 42 through which needle cannula 12 extends. Slot 42 preferably defines a width sufficient to receive at least distal portions of needle hub 18. In the unbiased condition of spring arm 32 corresponding to a ready-to-use condition of hypodermic syringe 20, link arm 38 projects proximally from hinge line 40 and at an acute angle to needle cannula 12. Link arm 38 defines a length "c" which is preferably approximately equal to or slightly greater than length "b" of spring arm 32. Thus, as depicted most clearly in FIGS. 1 and 2, link arm 38 projects proximally to a location approximately aligned with proximal end 34 of spring arm 32.

Needle point barrier 10 further includes a barrier arm 44 which is unitarily connected to link arm 38 along hinge 46. Hinge 46 extends substantially parallel to hinge 40, and both hinges 40 and 46 permit rotation about axes substantially orthogonal to needle cannula 12. Barrier arm 44 includes a distal end 48 spaced from hinge 46 by distance "d" which is preferably approximately equal to or slightly greater than the distances "b" and "c". Distal end 48 of barrier arm 42 includes a tip guard 50 unitarily molded therewith. More particularly, tip guard 50 includes a cylindrical aperture 52 extending therethrough and slidably surrounding needle cannula 12. Aperture 52, as best illustrated in FIG. 6, may include an undercut 53 adjacent distal end 48 for trapping and engaging distal end 16 of needle cannula 12 in the fully extended condition of needle point barrier 10, as explained and illustrated further below.

Barrier arm 44 projects proximally from hinge 46 to define a proximally facing finger actuator 54. Actuator 54 is of generally concave shape to conveniently receive a thumb or forefinger of a person using hypodermic syringe 20.

FIGS. 1 and 2 show needle point barrier 10 in a ready-to-use condition with spring arm 32 being planar, unbiased and aligned with the needle cannula 12. Link arm projects proximally at an acute angle to spring arm 32 such that portions of needle hub 18 are received in slot 42. Barrier arm 44 is substantially nested with link arm 38 such that tip guard 50 at distal end 48 of barrier arm 44 is substantially adjacent hinge 40 at distal end 36 of spring arm 32. In this Z-shaped condition, all of needle point barrier 10 is very close to hub 18 and luer collar 28, and hence will not visually or physically interfere with normal use of hypodermic syringe 20. Additionally, in this Z-shaped condition, all of needle point barrier 10 lies at the extreme proximal end of needle cannula 12, and hence enables clear visual observation of distal end 16. Thus, a health care worker can easily target a particular location on a patient for an injection, and can rotationally orient the bevel at distal end 16 of needle cannula 12.

After an injection is completed, the health care worker merely needs to exert a distally directed force on actuator 54 as illustrated by arrow "B" in FIG. 1. This force will cause simultaneous movement in all three arms of needle point barrier 10. In particular, barrier arm 44 will slide distally along needle cannula 12. This distal movement of barrier arm 44 will generate the simultaneous rotation of link arm 38 about hinges 40 and 46. Additionally, distal end 36 of spring arm 32 will deflect away from needle cannula 12 as shown in FIGS. 3 and 4. The health care worker exerting forces in direction "B" on actuator 54 must overcome the biasing forces exerted by the resilient material of spring arm 32. However, these forces are very small compared to the forces that can be generated by a thumb or forefinger of the hand holding hypodermic syringe 20.

After sufficient movement of barrier arm 44 in the distal direction, hinge 46 will become radially aligned with hinge 40 as illustrated in FIG. 3. Prior to this point, forces exerted by the health care worker will be opposed by the biasing forces exerted by spring arm 32. After the position illustrated in FIG. 3, biasing forces exerted by spring arm 32 will cooperate with and assist the distally directed forces exerted by the health care worker on actuator 54. In particular, biasing forces exerted by spring arm 32, as indicated by arrow "A" in FIG. 4, will work to propel barrier arm 44 distally, as indicated by arrow "C" in FIG. 4. As noted above, the biasing forces exerted by spring arm 32 are very small compared to the forces exerted by the finger of the health care worker. However, these same biasing forces exerted by spring arm 32 are very large compared to the minimal sliding resistance encountered by tip guard 50 on needle cannula 12. Hence, barrier arm 44 and tip guard 50 will be propelled rapidly toward distal end 16 of needle cannula 12.

The distal movement of barrier arm 44 will terminate abruptly when the three arms of needle point barrier 10 assume the approximately linear alignment shown in FIG. 5. The total length of needle point barrier 10 in the linear condition of FIG. 5 is selected to ensure that distal end 16 of needle cannula 12 is safely captured within tip guard 50.

Over extension of tip guard 50 beyond distal end 16 of needle cannula 12 should not occur. Additionally, any proximally directed forces on distal end 48 of barrier arm 44 will cause distal end 16 to bite into undercut 53 of aperture 52 through tip guard 50. In any event, these proximally directed forces on the linearly aligned arms of needle point barrier 10 will not generate a foldable collapsing that would be required to re-expose distal end 16 of needle cannula 12.

There may be applications where it is desirable for the needle point barrier to move between the extended position where the distal end of the barrier arm shields the distal end of the needle to a ready-to-use or retracted position where the distal end of the needle is re-exposed. Accordingly, a non-locking tip guard is within the purview of the present invention. However, the preferred embodiment, as best illustrated in FIG. 6, includes means for preventing the needle point barrier from moving from the extended position. Such means includes undercut 53 in cylindrical aperture 52 of tip guard 50. The cylindrical aperture can be sized to offer a little clearance between itself and the outside diameter of the needle cannula so that when the distal end of the needle is within the tip guard, any attempt to move the tip guard in a proximal direction will cause the distal end of the needle to embed itself, due to misalignment, into the undercut portion of the tip guard. Thus preventing movement of the barrier arm from the extended position.

An alternative means for preventing movement of the barrier arm from the extended position is illustrated in FIG. 7. The embodiment of FIG. 7 is the same in every respect to the embodiment of FIGS. 1–6 with the exception of the tip guard which contains an alternate structure to prevent movement of the barrier arm from the extended position. In particular, barrier arm 70 includes tip guard 72 and needle receiving aperture 74 extending therethrough. Tip guard 72 further includes spring lock 76 formed of resilient, puncture-resistant material such as spring metal. In this embodiment the spring lock includes a bent mounting portion 78 which is frictionally embedded in receiving slot 79 of the tip guard. A needle engaging portion 80 of the spring lock is biased against needle cannula 12. The needle receiving aperture and the spring lock are configured so that the tip guard is axially movable along the needle cannula. However, when the tip guard is in the extended position the distal end of the needle cannula is behind front wall 81 of distal end 73 of the tip guard, so that spring lock 76 can move across the aperture wherein needle engaging portion 80 of the spring lock blocks the aperture in front wall 81, preventing the barrier arm from moving from the extended position, to expose the distal end of the needle cannula. It is understood that there are many ways to prevent movement of the barrier arm from the extended position and the means described herein are representative of these many possibilities. Means for preventing movement of the barrier from the extended position can include a torturous aperture in the tip guard which will prevent the distal end of the needle from passing therethrough in a distal direction. A spherical metal ball may be used to block the aperture after the needle is withdrawn into the tip guard. Also, two of the arms of the needle guard can contain cooperating structure to lock together when the barrier arm is in the extended position, for example, the link arm and the barrier arm can be configured to lock together in the extended position to prevent movement of the barrier arm from the extended position.

As noted above, the needle point barrier of the present invention offers several structural and functional advantages. First, the needle point barrier is single-handedly actuatable from a position proximally of the sharp point of needle cannula 12. Hence, accidental contact with the needle during shielding is avoided. Second, after an initial manual activation, needle point barrier 10 is substantially self-propelling toward a fully shielded condition. Third, elements of needle point barrier 10 are unbiased both in the ready-to-use or retracted position and in the fully shielded condition. No stored energy exists in any components of needle point barrier. Hence, needle point barrier can be reliably formed from many different materials, including plastics. Finally, needle point barrier efficiently nests upon itself in a Z-shaped ready-to-use condition so as to be visually and physically unobtrusive by not blocking the user's view or access to the injection site.

What is claimed is:

1. A needle point barrier comprising:

a needle cannula having a proximal end and a distal end;

a spring arm having a proximal end secured adjacent said proximal end of said needle cannula and a distal end projecting toward said distal end of said needle cannula, said distal end of said spring arm being resiliently deflectable away from said needle cannula;

a link arm hingedly connected to said distal end of said spring arm; and a barrier arm having a proximal end hingedly connected to a location on said link arm remote from said spring arm and a distal end slidably engaged with said needle cannula, said needle point barrier being nested in a Z-shape with said distal end of said barrier arm being substantially adjacent said distal end of said spring arm, said barrier arm being movable to an extended position where said distal end of said barrier arm shields said distal end of said needle cannula, said spring arm being deflected away from said needle cannula during a first portion of said movement of said barrier arm toward said extended position and resiliently returning toward an undeflected condition for propelling said barrier arm to said distal end of said needle cannula during a second portion of said movement.

2. The needle point barrier of claim 1, wherein said spring arm, said link arm and said barrier arm are formed from a unitary piece of metallic material.

3. The needle point barrier of claim 2, wherein said proximal end of said needle cannula is securely embedded in a needle hub, said proximal end of said spring arm being securely connected to said needle hub.

4. The needle point barrier of claim 1, wherein, said spring arm, said link arm and said barrier arm are unitarily molded from a plastic material.

5. The needle point barrier of claim 4, wherein said proximal end of said needle cannula is securely embedded in a needle hub, said proximal end of said spring arm being securely joined to said needle hub.

6. The needle point barrier of claim 5, wherein said spring arm is unitary with said needle hub.

7. The needle point barrier of claim 1, wherein said spring arm is aligned substantially parallel to said needle cannula and in an unbiased condition when said needle point barrier is nested in said Z-shaped configuration.

8. The needle point barrier of claim 1, wherein said link arm is formed with an elongate slot therein, said needle cannula passing through said slot of said link arm.

9. The needle point barrier of claim 1, further including an actuator projecting proximally from said hinged connection between said barrier arm and said link arm.

10. The needle point barrier of claim 1 further including means for preventing movement of the barrier arm from the extended position.

11. The needle point barrier of claim 1, wherein said distal end of said barrier arm defines a tip guard surrounding said needle cannula and slidably engaged therewith.

12. The needle point barrier of claim 11, further including means for preventing movement of the barrier arm from the extended position.

13. A needle point barrier comprising:

a needle cannula having a proximal end and a distal end;

a resilient spring arm having a proximal end secured substantially adjacent said proximal end of said needle cannula and a distal end projecting toward said distal end of said needle cannula;

a link arm hingedly connected to said distal end of said spring arm and projecting proximally toward said proximal end of said needle cannula;

a barrier arm having opposed proximal end distal ends, said proximal end of said barrier arm being hingedly connected to a location on said link arm remote from said spring arm;

a tip guard disposed on said distal end of said barrier arm, said tip guard being slidably engaged with said needle cannula and disposed substantially adjacent said distal end of said spring arm; and a proximally facing actuator surface substantially adjacent said hinged connection of said barrier arm and said link arm, for moving said barrier arm and said tip guard distally, said distal end of said spring arm deflecting away from said needle cannula during initial distal movement of said barrier arm, said spring arm resiliently returning toward an undeflected condition after said proximal end of said barrier arm moves distally beyond said spring arm, such that said resilient return of said spring arm toward an undeflected condition propels said barrier arm distally and into a position where said tip guard protectively surrounds said distal end of said needle cannula.

14. The needle point barrier of claim 13, wherein said spring arm, said link arm and said barrier arm are unitary with one another.

15. The needle point barrier of claim 14, wherein said spring arm, said link arm and said barrier arm are unitarily molded from a plastic material.

16. The needle point barrier of claim 15, wherein said needle cannula includes a needle hub securely engaged with said proximal end thereof, said needle hub being molded from a plastic material and being unitary with said spring arm of said needle point barrier.

17. The needle point barrier of claim 14, wherein said spring arm, said link arm and said barrier arm are unitarily formed from a metallic material.

18. The needle point barrier of claim 13, wherein said link arm includes an elongate slot formed therein, said needle cannula projecting through said slot.

19. The needle point barrier of claim 13, wherein said hinged connections of said link arm to said spring arm and said barrier arm are parallel to one another and perpendicular to said needle cannula.

20. The needle point barrier of claim 13 further including means for preventing movement of the tip guard from said position wherein said tip guard protectively surrounds the distal end of said needle cannula.

* * * * *